US010519452B2

(12) United States Patent
Choi et al.

(10) Patent No.: US 10,519,452 B2
(45) Date of Patent: *Dec. 31, 2019

(54) ANTIVIRAL AGENT COMPRISING RNA OLIGONUCLEOTIDE

(71) Applicant: KOREA ADVANCED INSTITUTE OF SCIENCE AND TECHNOLOGY, Daejeon (KR)

(72) Inventors: Byong-Seok Choi, Daejeon (KR); Janghyun Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/310,559

(22) PCT Filed: Aug. 29, 2016

(86) PCT No.: PCT/KR2016/009601
§ 371 (c)(1),
(2) Date: Apr. 20, 2017

(87) PCT Pub. No.: WO2017/065405
PCT Pub. Date: Apr. 20, 2017

(65) Prior Publication Data
US 2017/0240897 A1 Aug. 24, 2017

(30) Foreign Application Priority Data

Oct. 15, 2015 (KR) .................. 10-2015-0144306
Apr. 11, 2016 (KR) .................. 10-2016-0044080
Aug. 1, 2016 (KR) .................. 10-2016-0098129

(51) Int. Cl.
C07H 21/04 (2006.01)
C12N 15/117 (2010.01)
A61K 31/713 (2006.01)
C12N 15/113 (2010.01)

(52) U.S. Cl.
CPC .......... *C12N 15/117* (2013.01); *A61K 31/713* (2013.01); *C12N 15/113* (2013.01); *C12N 15/1131* (2013.01); *C12N 2310/17* (2013.01); *C12N 2310/31* (2013.01); *C12N 2310/315* (2013.01); *C12N 2310/531* (2013.01); *Y02A 50/385* (2018.01); *Y02A 50/393* (2018.01)

(58) Field of Classification Search
CPC ...................................... C07H 21/04
See application file for complete search history.

(56) References Cited

U.S. PATENT DOCUMENTS

| 7,691,997 B2 * | 4/2010 | Khvorova ............ A61K 31/713 536/24.5 |
| 2004/0170963 A1 | 9/2004 | Su et al. ........................ 435/5 |
| 2012/0121551 A1 | 5/2012 | Hartmann et al. .......... 494/93.7 |
| 2012/0251571 A1 | 10/2012 | Silverman et al. |
| 2015/0148530 A1 * | 5/2015 | McSwiggen ........ C12N 15/1131 536/24.5 |
| 2017/0051056 A1 * | 2/2017 | Naka ................. G01N 33/57449 |

FOREIGN PATENT DOCUMENTS

| KR | 10-2005-0084693 | 8/2005 | ............ A61K 48/00 |
| WO | WO 2013/162350 | 10/2013 | ............ C12N 15/11 |

OTHER PUBLICATIONS

Samuel, C.E. (Nature Biotech., vol. 22, No. 3, pp. 280-282 (2004)).*
Kim et al (Nature Biotech., vol. 22, No. 3, pp. 321-325 (2004)).*
Andrejeva, et al. (2013) "ISG56/IFIT1 is primarily responsible for interferon-induced changes to patterns of parainfluenza virus type 5 transcription and protein synthesis." *Journal of General Virology*, 94:59-68.
Ma, et al. (2007) "RNA interference and antiviral therapy." *World J Gastroenterol*, 13(39):5169-5179, Oct. 21, 2007.
International Search Report, dated Dec. 8, 2016 issued in International Patent Application No. PCT/KR2016/009601, with English Translation.
Extended European Search Report from corresponding European Patent Application No. 16798376.6, dated Feb. 9, 2018.

* cited by examiner

*Primary Examiner* — Kimberly Chong
(74) *Attorney, Agent, or Firm* — Harness, Dickey & Pierce, P.L.C.

(57) ABSTRACT

The present invention provides an antiviral agent comprising an RNA oligonucleotide having a particular sequence and structure. Specifically, when a cell line is treated with an RNA oligonucleotide having specific sequence and helical bend structure according to the present invention, the expression of interferon-β or ISG56 is increased and antiviral activating is exhibited. Thus, a composition comprising the RNA oligonucleotide can be used as an antiviral agent.

20 Claims, 10 Drawing Sheets

Specification includes a Sequence Listing.

SEQUENCE LISTING

<160> NUMBER OF SEQ ID NOS: 20

<210> SEQ ID NO 1
<211> LENGTH: 8
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (7)..(8)
<223> OTHER INFORMATION: n is a, c, g, or u

<400> SEQUENCE: 1 nguagann                                                                 8

<210> SEQ ID NO 2
<211> LENGTH: 8
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u

<400> SEQUENCE: 2 nnuuugcn                                                                 8

<210> SEQ ID NO 3
<211> LENGTH: 8
<212> TYPE: RNA
<213> ORGANISM: Artificial Sequence
<220> FEATURE:
<223> OTHER INFORMATION: RNA oligonucleotide

<400> SEQUENCE: 3 gguagacg                                                                 8

<210> SEQ ID NO 4
<211> LENGTH: 8
<212> TYPE: RNA
<213> ORGANISM: Artificial Sequence
<220> FEATURE:
<223> OTHER INFORMATION: RNA oligonucleotide

<400> SEQUENCE: 4 cguuugcc                                                                 8

<210> SEQ ID NO 5
<211> LENGTH: 34
<212> TYPE: RNA
<213> ORGANISM: Artificial Sequence
<220> FEATURE:
<223> OTHER INFORMATION: control RNA oligonucleotide

<400> SEQUENCE: 5
gagcagaaac aaggcuucgg ccuuguuucu gcuc                                   34

```
<210> SEQ ID NO 6
<211> LENGTH: 33
<212> TYPE: RNA
<213> ORGANISM: Artificial Sequence
<220> FEATURE:
<223> OTHER INFORMATION: iav RNA oligonucleotide

<400> SEQUENCE: 6
gaguagaaac aaggcuucgg ccugcuuuug cuc                           33

<210> SEQ ID NO 7
<211> LENGTH: 80
<212> TYPE: RNA
<213> ORGANISM: Artificial Sequence
<220> FEATURE:
<223> OTHER INFORMATION: Int-NS1 RNA oligonucleotide

<400> SEQUENCE: 7
aguagaaaca aggguguuuu uuauuauuaa auaagcugaa guguuuggau ccauuauguc    60
uuugucaccc ugcuuuugcu                                              80

<210> SEQ ID NO 8
<211> LENGTH: 32
<212> TYPE: RNA
<213> ORGANISM: Artificial Sequence
<220> FEATURE:
<223> OTHER INFORMATION: Bend-GC RNA oligonucleotide

<400> SEQUENCE: 8
gguagacgcg cgcguucgcg cgcgcguuug cc                            32

<210> SEQ ID NO 9
<211> LENGTH: 20
<212> TYPE: RNA
<213> ORGANISM: Artificial Sequence
<220> FEATURE:
<223> OTHER INFORMATION: Cont-GC-8bp RNA oligonucleotide

<400> SEQUENCE: 9
ggcagacguu cgcgucugcc                                          20

<210> SEQ ID NO 10
<211> LENGTH: 20
<212> TYPE: RNA
<213> ORGANISM: Artificial Sequence
<220> FEATURE:
<223> OTHER INFORMATION: Bend-GC-8bp RNA oligonucleotide

<400> SEQUENCE: 10
gguagacguu cgcguuugcc                                          20

<210> SEQ ID NO 11
<211> LENGTH: 18
<212> TYPE: DNA
<213> ORGANISM: Artificial Sequence
<220> FEATURE:
<223> OTHER INFORMATION: interferon-beta forward primer

<400> SEQUENCE: 11
ggaggacgcc gcattgac                                            18

<210> SEQ ID NO 12
<211> LENGTH: 24
<212> TYPE: DNA
<213> ORGANISM: Artificial Sequence
<220> FEATURE:
```

<223> OTHER INFORMATION: interferon-beta reverse primer

<400> SEQUENCE: 12
caatagtctc attccagcca gtgc                                                24

<210> SEQ ID NO 13
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 13
gcattgccct caacgaccac                                                     20

<210> SEQ ID NO 14
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 14
gaggccatgt gggccatgag                                                     20

<210> SEQ ID NO 15
<211> LENGTH: 22
<212> TYPE: DNA
<213> ORGANISM: Artificial Sequence
<220> FEATURE:
<223> OTHER INFORMATION: ISG56 forward primer

<400> SEQUENCE: 15
gcctccttgg gttcgtctac aa                                                  22

<210> SEQ ID NO 16
<211> LENGTH: 22
<212> TYPE: DNA
<213> ORGANISM: Artificial Sequence
<220> FEATURE:
<223> OTHER INFORMATION: ISG56 reverse primer

<400> SEQUENCE: 16
tcaaagtcag cagccagtct ca                                                  22

<210> SEQ ID NO 17
<211> LENGTH: 16
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (7)..(10)
<223> OTHER INFORMATION: n is a, c, g, or u
<220> FEATURE:
<221> NAME/KEY: misc_feature
<222> LOCATION: (16)..(16)
<223> OTHER INFORMATION: n is a, c, g, or u

<400> SEQUENCE: 17
nguagannnn uuugcn                                                         16

```
<210> SEQ ID NO 18
<211> LENGTH: 16
<212> TYPE: RNA
<213> ORGANISM: Artificial Sequence
<220> FEATURE:
<223> OTHER INFORMATION: RNA oligonucleotide

<400> SEQUENCE: 18
gguagacgcg uuugcc                                                        16

<210> SEQ ID NO 19
<211> LENGTH: 89
<212> TYPE: RNA
<213> ORGANISM: Artificial Sequence
<220> FEATURE:
<223> OTHER INFORMATION: Long_Bend RNA oligonucleotide

<400> SEQUENCE: 19
gguagacgaa accagauaaa aaaaaaaaaa aaaaaaaaaa aaauaauuuu uuuuuuuuuu        60
uuuuuuuuuu uuaucugguu ucguuugcc                                          89

<210> SEQ ID NO 20
<211> LENGTH: 71
<212> TYPE: RNA
<213> ORGANISM: Artificial Sequence
<220> FEATURE:
<223> OTHER INFORMATION: Long_Bend Short RNA oligonucleotide

<400> SEQUENCE: 20
gguagacgaa aaaaaaaaaa aaaaaaaaaa aaaauaauuu uuuuuuuuu uuuuuuuuu          60 uuucguuugc c                                                             71
```

ANTIVIRAL AGENT COMPRISING RNA OLIGONUCLEOTIDE

CROSS-REFERENCE TO RELATED APPLICATIONS

This application is a national phase application of PCT Application No. PCT/KR2016/009601, filed on Apr. 8, 2015, which claims the benefit of Korean Patent Application No. 10-2016-0098129, filed Aug. 1, 2016, which claims priority to Korean Patent Application No. 10-2016-0044080, filed Apr. 11, 2016 which claims the benefit and priority of Korean Patent Application No. 10-2015-0144306, filed Oct. 15, 2015. The entire disclosures of the applications identified in this paragraph are incorporated herein by reference.

FIELD

The present invention relates to an antiviral agent comprising an RNA oligonucleotide having a particular sequence and structure.

BACKGROUND

Interferon is a glycoprotein derived from most of the cells having a nucleus, and has antiviral property by inhibiting proliferation of viruses. Interferon elicits a series of intracellular responses and immunoregulatory responses by binding to a specific receptor on the cell membrane of the cell surface. The intracellular responses may include induction of the activation of specific enzymes, etc., and the immunoregulatory responses may include enhancing the phagocytosis activity of macrophages, increasing the cytotoxicity of lymphocytes against target cells, and inhibiting proliferation of viruses in virus-infected cells, etc.

Interferons are classified into type 1 and type 2 based on the physiochemical and functional properties. Type 1 interferons include interferon-α, -β, -τ, and -ω; and type 2 interferons include interferon-γ. Among them, interferon-β is a protein of a single chain, which has a molecular weight of approximately 20 kDa, contains a sugar of about 20%, and is composed of 166 amino acids.

Currently, recombinant interferon-β is used along with interferon-α as a therapeutic agent for disorders caused by various viruses such as hepatitis B virus and hepatitis C virus. It was reported that the recombinant interferon-β can be used as an immune adjuvant for inhibiting the recurrence of papilloma virus infection (Gross G. et al., *Dermatology*, 1998; 196(3):330-4).

Recently, researches have been made to enhance immune responses and treat various disorders by using an RNA oligonucleotide. U.S. Patent Application Publication No. 2012/0288476 discloses that an uncapped oligonucleotide having a phosphate group at the 5'-end can increase the expression of type 1 interferon, interleukin-18, and interleukin-1β, etc, suggesting its use as an antiviral agent.

In addition, U.S. Patent Application Publication No. 2012/0121551 discloses that an RNA consisting of four nucleotides can promote immune responses by inducing the activation of interferon-α, suggesting its use for treating a disorder.

The RNAs mentioned above have a common feature that they all have a triphosphate group at the 5'-end. It has been known in the art that an uncapped RNA which has a triphosphate group at the 5'-end can activate the expression of interferon by binding to intracellular retinoic acid-inducible gene-I (RIG-I) protein.

DISCLOSURE OF INVENTION

Technical Problem

The present inventors have endeavored diligently to find a substance which can increase the expression of interferon-β or interferon stimulated gene 56 (ISG56) expressed by interferon-β, and surprisingly and unexpectedly discovered that an RNA oligonucleotide which does not have a triphosphate group at the 5'-end can also increase the expression of interferon-β or ISG56 if the RNA oligonucleotide has a particular sequence and structure, and shows antiviral activity. Thus, such RNA oligonucleotide can be used as an antiviral agent.

An object of the present invention is to provide an antiviral agent comprising an RNA oligonucleotide having a particular sequence and structure.

Another object of the present invention is to provide a method for treating a viral disorder using an RNA oligonucleotide having a particular sequence and structure.

Another object of the present invention is to provide use of an RNA oligonucleotide having a particular sequence and structure for treating a viral disorder.

Solution to Problem

The present invention provides an antiviral agent comprising an RNA oligonucleotide as an active ingredient, wherein the RNA oligonucleotide comprises the base sequence represented by SEQ ID NO:1 (5'-$N_1$GUA-GA$N_2N_3$-3') and the base sequence represented by SEQ ID NO:2 (5'-$N_4N_5$UUUGC$N_6$-3') wherein the base sequences are bound to each other by a complementary binding to form double strands having a helical bend structure; and the base sequences represented by SEQ ID NO:1 and SEQ ID NO:2 have a hydroxy (OH) group at the 5'-end thereof.

The present invention also provides an antiviral agent comprising an RNA oligonucleotide as an active ingredient, wherein the RNA oligonucleotide comprises the base sequence represented by SEQ ID NO:1 (5'-$N_1$GUA-GA$N_2N_3$-3') and the base sequence represented by SEQ ID NO:2 (5'-$N_4N_5$UUUGC$N_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

The present invention also provides an antiviral agent comprising an RNA oligonucleotide as an active ingredient, wherein the RNA oligonucleotide comprises the base sequence represented by SEQ ID NO:17 (5'-$N_1$GUA-GA$N_2N_3N_4N_5$UUUGC$N_6$-3) formed by connecting the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein two base sequences represented by SEQ ID NO:17 are bound to each other by a complementary binding to form double strands having a helical bend structure; and the base sequence represented by SEQ ID NO:17 has a hydroxy (OH) group at the 5'-end thereof.

The present invention also provides an antiviral agent comprising an RNA oligonucleotide as an active ingredient, wherein the RNA oligonucleotide comprises the base sequence represented by SEQ ID NO:17 (5'-

$N_1GUAGAN_2N_3N_4N_5UUUGCN_6$-3') formed by connecting the base sequence represented by SEQ ID NO:1 (5'-$N_1GUAGAN_2N_3$-3') and the base sequence represented by SEQ ID NO:2 (5'-$N_4N_5UUUGCN_6$-3') wherein first and second base sequences represented by SEQ ID NO:17 are bound to each other by a complementary binding to form double strands having a helical bend structure; the 3'-end of the first base sequence represented by SEQ ID NO:17 and the 5'-end of the second base sequence represented by SEQ ID NO:17 are connected into a loop to form a hairpin structure; and the first base sequence represented by SEQ ID NO:17 has a hydroxy (OH) group at the 5'-end thereof.

The present invention also provides a method for treating a viral disorder which comprises administering one of the aforementioned RNA oligonucleotides to a subject in need of such treatment.

The present invention also provides use of one of the aforementioned RNA oligonucleotides for the preparation of a therapeutic agent for a viral disorder, Advantageous Effects When a cell line is treated with an RNA oligonucleotide having specific sequence and helical bend structure according to the present invention, the expression of interferon-β or ISG56 is increased and antiviral activity is exhibited. Thus, a composition comprising such RNA oligonucleotide can be used as an antiviral agent.

MODE FOR THE INVENTION

Figure 1:
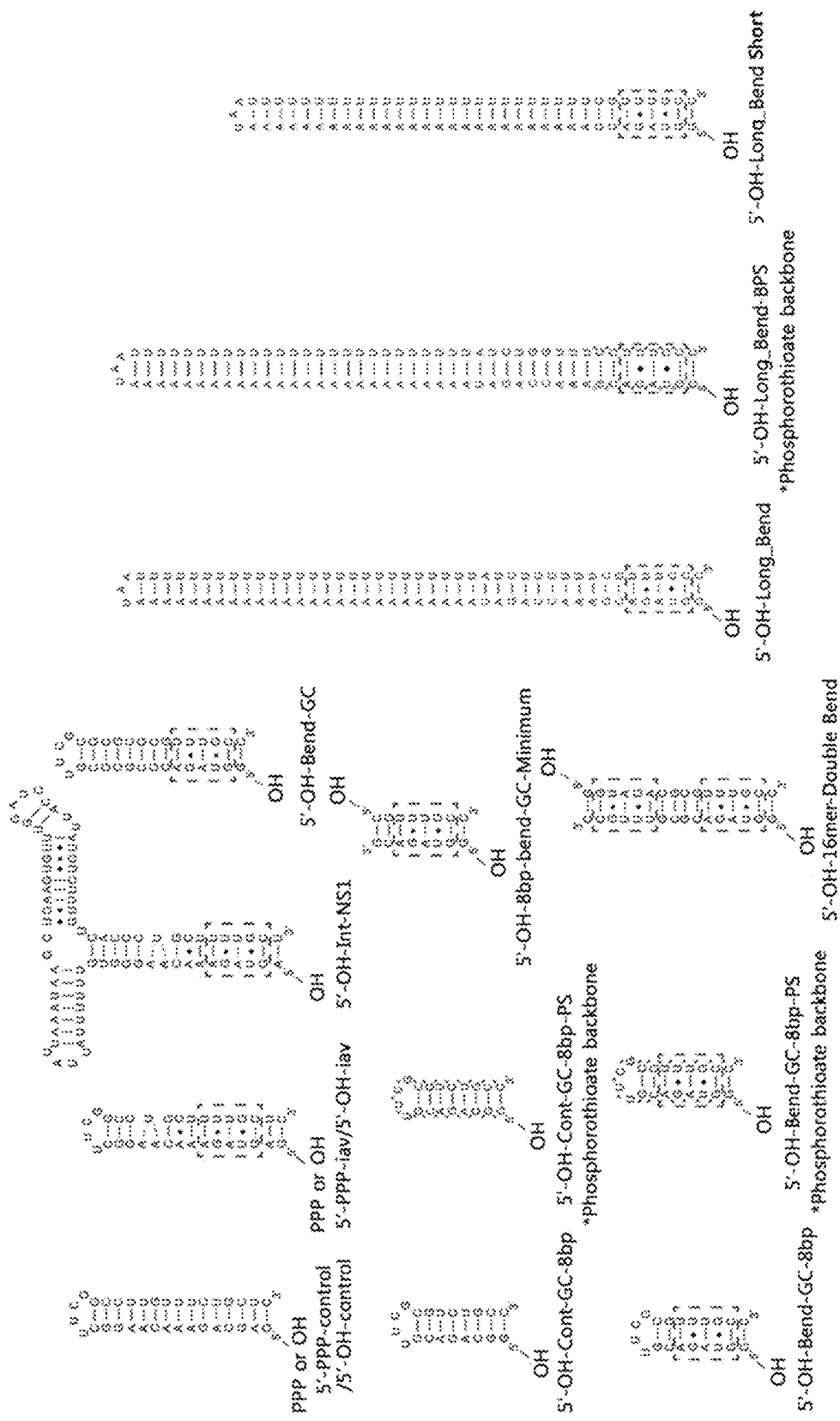
FIG. 1 shows the sequences and structures of RNA oligonucleotides prepared according to an example of the present invention.

Hereinafter, the present invention will be described in detail.

The present invention provides an antiviral agent comprising an RNA oligonucleotide as an active ingredient, wherein the RNA oligonucleotide comprises the base sequence represented by SEQ ID NO:1 (5'-$N_1GUAGAN_2N_3$-3') and the base sequence represented by SEQ ID NO:2 (5'-$N_4N_5UUUGCN_6$-3') wherein the base sequences are bound to each other by a complementary binding to form double strands having a helical bend structure; and the base sequences represented by SEQ ID NO:1 and SEQ ID NO:2 have a hydroxy (OH) group at the 5'-end thereof.

An RNA oligonucleotide according to the present invention may have 8 to 100, 8 to 50, 8 to 30, 8 to 20, 10 to 100, 10 to 50, 10 to 30, 20 to 500, 20 to 300, 10 to 200, 10 to 100, or 20 to 50 bases. An RNA oligonucleotide in one example of the present invention may have 8 to 16 bases when it is a single strand, while it may have 16 to 32 bases when double strands.

In the base sequence represented by SEQ ID NO:1 or SEQ ID NO:2 which forms the RNA oligonucleotide, $N_1$ to $N_6$ may be one selected from the group consisting of A, G, C and U. Specifically, $N_1$ to $N_6$ may be G or C. In one example of the present invention, $N_1$ may be G, $N_2$ may be C, and $N_3$ may be G in the base sequence represented by SEQ ID NO:1 (corresponding to SEQ ID NO:3); and $N_4$ may be C, $N_5$ may be G, and $N_6$ may be C in the base sequence represented by SEQ ID NO:2 (corresponding to SEQ ID NO:4).

When the RNA oligonucleotide having such base sequence forms double strands, the third base (U) and the fifth base (G) of the base sequence represented by SEQ ID NO:1 and the sixth base (G) and the fourth base (U) of the base sequence represented by SEQ ID NO:2 respectively form wobble base pairs, or non-Watson-Crick base pairs.

An RNA oligonucleotide of the present invention may form a helical bend structure between the fourth base (A) of the base sequence represented by SEQ ID NO:1 and the fifth base (U) of the base sequence represented by SEQ ID NO:2.

In one example of the present invention, the helical bend structure is formed between the fourth base (A) of the base sequence represented by SEQ ID NO:1 and the fifth base (U) of the base sequence represented by SEQ ID NO:2 when the third base (U) and the fifth base (G) of the base sequence represented by SEQ ID NO:1 and the sixth base (G) and the fourth base (U) of the base sequence represented by SEQ ID NO:2 respectively form wobble base pairs.

The helical bend structure may have a shape bent in 10 to 90 degrees relative to the plane formed by the double-stranded RNA, particularly 30 to 70 degrees, and more particularly 40 to 50 degrees.

In the RNA oligonucleotide according to the present invention, at least one of the phosphodiester bonds in the RNA oligonucleotide may be changed to at least one selected from the group consisting of a phosphorothioate bond, a boranophosphate bond and a methylphosphonate bond, in order to inhibit degradation by endonuclease and improve in vivo stability. In a specific example of the present invention, at least one of the phosphodiester bonds may be changed to the phosphorothioate bond.

Also, the present invention provides an antiviral agent comprising an RNA oligonucleotide as an active ingredient, wherein the RNA oligonucleotide comprises the base sequence represented by SEQ ID NO:1 (5'-$N_1GUAGAN_2N_3$-3) and the base sequence represented by SEQ ID NO:2 (5'-$N_4N_5UUUGCN_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

An RNA oligonucleotide having the hairpin structure of the present invention may have the characteristics described above. Also, a phosphodiester bond constituting the RNA oligonucleotide may be substituted with a phosphorothioate bond. The phosphorothioate bond may be formed between all nucleotides constituting the RNA oligonucleotide or between the nucleotides constituting the base sequences represented by SEQ ID NO:1 and SEQ ID NO:2.

In the hairpin structure, the loop may be composed of 4 to 80, 4 to 75, 4 to 70, 4 to 65, 4 to 60, 4 to 55, 4 to 50, 4 to 45, 4 to 40, 4 to 35, 4 to 30, 4 to 25, 4 to 20, 4 to 15, or 4 to 10 bases. In one example of the present invention, the loop may be composed of 4, 15, 16, 55, 64 or 73 bases. In one example of the present invention, the four bases constituting the loop may be UUCG.

Also, if some of the base sequences constituting the loop are complementary to each other, they may form a stem structure by Watson-Crick base pairing. The stem structure may include AU motif in which A and U forms a Watson-Crick base pair.

Herein, the AU motif may be composed of 10 to 50, 15 to 40, 20 to 35, or 25 to 30 AU base pairs. In an example of the present invention, the AU motif may be composed of 26 consecutive AU base pairs.

In one example of the present invention, the RNA oligonucleotide having the hairpin structure may be the base sequence represented by SEQ ID NO:6, SEQ ID NO:7, SEQ ID NO:8, SEQ ID NO:10, SEQ ID NO:19 or SEQ ID NO:20.

Also, the present invention provides an antiviral agent comprising an RNA oligonucleotide as an active ingredient, wherein the RNA oligonucleotide comprises the base sequence represented by SEQ ID NO:17 (5'-$N_1GUAGAN_2N_3N_4N_5UUUGCN_6$-3) formed by connecting the base sequence represented by SEQ ID NO:1 (5'-$N_1GUAGAN_2N_3$-3) and the base sequence represented by SEQ ID NO:2 (5'-$N_4N_5UUUGCN_6$-3') wherein two base sequences represented by SEQ ID NO:17 are bound to each other by a complementary binding to form double strands having a helical bend structure; and the base sequence represented by SEQ ID NO:17 has a hydroxy (OH) group at the 5'-end thereof.

Specifically, the RNA oligonucleotide may have two base sequences represented by SEQ ID NO:17 with a palindromic structure. The term "palindromic structure" refers to a structure in which two base sequences constituting double strands are composed of identical base sequence when read from the 5'- to 3'-end. In the present invention, such palindromic structure may be double strands in which the 3'-end of the base sequence represented by SEQ ID NO:1 and the 5'-end of the base sequence represented by SEQ ID NO:2 are connected to form a single strand, and such two single strands are bound to each other by a complementary binding to form double strands. In one example of the present invention, such single strand may be a base sequence represented by SEQ ID NO:18.

The double stranded RNA oligonucleotide having the palindromic structure may have two helical bend structures.

Also, the RNA oligonucleotide having the palindromic structure may have the characteristics described above. A phosphodiester bond constituting the RNA oligonucleotide may be substituted with another bond described above.

Also, the present invention provides an antiviral agent comprising an RNA oligonucleotide as an active ingredient, wherein the RNA oligonucleotide comprises the base sequence represented by SEQ ID NO:17 (5'-$N_1GUAGAN_2N_3N_4N_5UUUGCN_6$-3) formed by connecting the base sequence represented by SEQ ID NO:1 (5'-$N_1GUAGAN_2N_3$-3') and the base sequence represented by SEQ ID NO:2 (5'-$N_4N_5UUUGCN_6$-3') wherein first and second base sequences represented by SEQ ID NO:17 are bound to each other by a complementary binding to form double strands having a helical bend structure; the 3'-end of the first base sequence represented by SEQ ID NO:17 and the 5'-end of the second base sequence represented by SEQ ID NO:17 are connected into a loop to form a hairpin structure; and the first base sequence represented by SEQ ID NO:17 has a hydroxy (OH) group at the 5'-end thereof.

The RNA oligonucleotide with the hairpin structure may have the palindromic structure described above, and two helical bend structures. Such RNA oligonucleotide may have the characteristics described above. Also, a phosphodiester bond constituting the RNA oligonucleotide may be substituted with another bond described above.

The present inventors have prepared RNA oligonucleotides having a double-stranded RNA or hairpin RNA structure (FIG. 1). Among them, 5'-OH-iav or 5'-PPP-iav were found to have a helical bend structure (FIG. 2) and to increase the expression of interferon-β and ISG56 (FIGS. 3 to 8).

Figure 9:
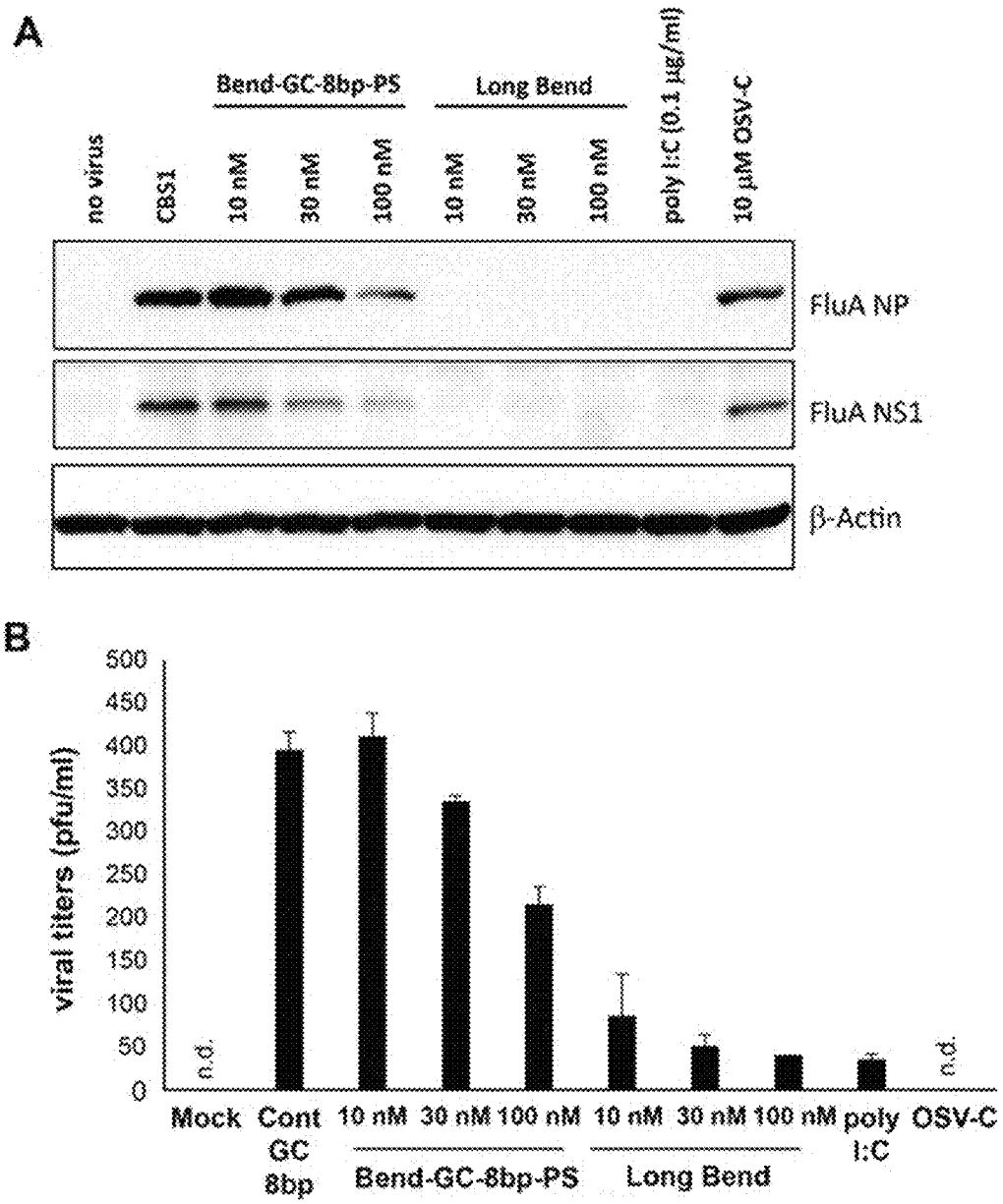
FIG. 9 shows the antiviral activity against influenza A virus of 5'-OH-Bend-GC-8 bp-PS and 5'-OH-Long_Bend, RNA oligonucleotides prepared according to an example of the present invention, verified by Western blot (A) and a plaque assay (B).
Figure 10:
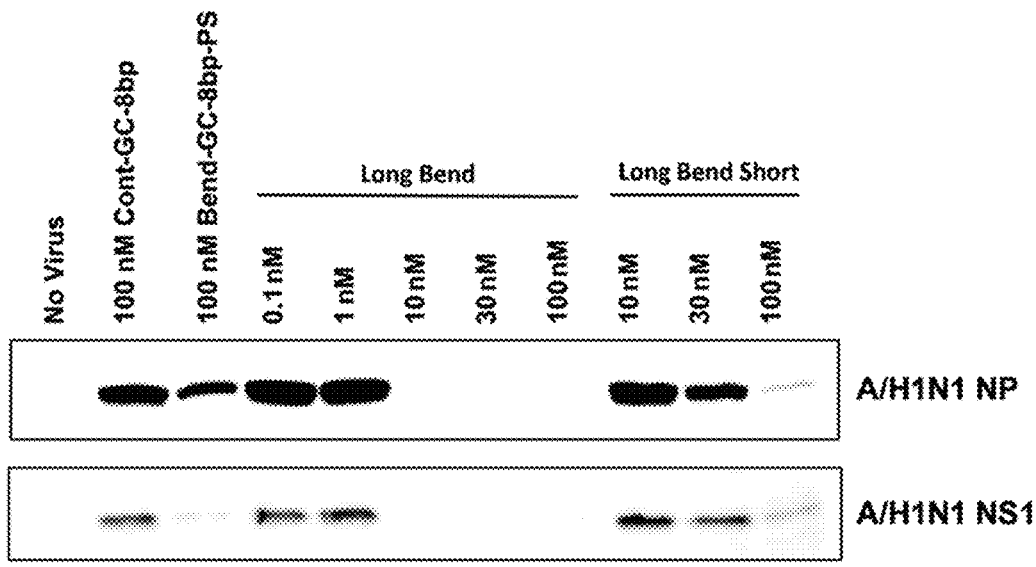
FIG. 10 shows the antiviral activity against influenza A virus of 5'-OH-Long_Bend Short, an RNA oligonucleotide prepared according to an example of the present invention, verified by Western blot.
Figure 11:
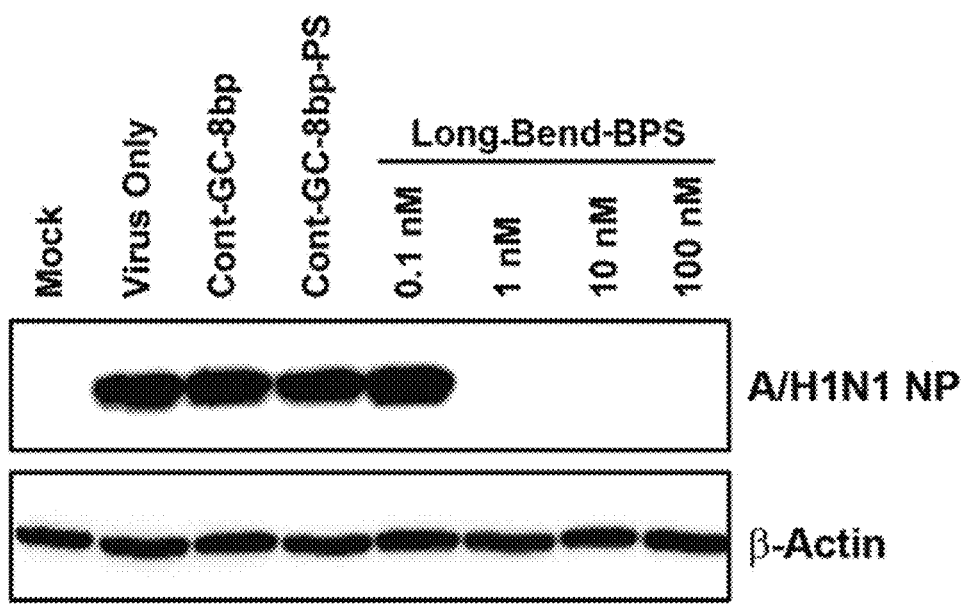
FIG. 11 shows the antiviral activity against influenza A virus of 5'-OH-Long_Bend-BPS, an RNA oligonucleotide prepared according to an example of the present invention, verified by Western blot.

Also, an RNA oligonucleotide having the helical bend structure was found to show an antiviral activity against influenza A virus (FIGS. 9 to 11).

Accordingly, an RNA oligonucleotide having a helical bend structure of the present invention increases the expression of interferon-β and ISG56, and shows an antiviral activity. Thus it can be used as an antiviral agent.

For example, an antiviral agent according to the present invention can be used for inhibiting the activity of viruses which have RNA as a gene. Specific examples of such RNA viruses include hepatitis C virus, Dengue virus, acute respiratory syndrome virus, Middle East respiratory syndrome coronavirus, influenza virus, West Nile virus, Ebola virus, vesicular stomatitis virus, Newcastle Disease virus, etc.

Also, the antiviral agent can be used for inhibiting the activity of viruses which have DNA as a gene. Specific examples of such DNA viruses include hepatitis B virus.

The aforementioned antiviral agent may comprise an RNA oligonucleotide of the present invention as an active ingredient in an amount of 10 to 95 weight % based on the total weight of the antiviral agent. In addition, an antiviral agent of the present invention may comprise one or more other active ingredients with the same or similar function in addition to the aforementioned active ingredient.

An antiviral agent of the present invention may comprise one or more pharmaceutically acceptable carriers for the administration in addition to the aforementioned active ingredient.

The dosage of an antiviral agent of the present invention may be adjusted based on various factors such as type and severity of a disease, type and amount of an active ingredient and other ingredients comprised in the composition, type of a formulation, and age, weight, general health condition, sex and diet of the patient, time of administration, route of administration, treatment period, and drugs simultaneously used, etc. However, to achieve a desired effect, the effective amount of an RNA oligonucleotide comprised in an antiviral agent of the present invention is adjusted to reach the intracellular concentration of 1 to 1,000 nM, specifically 100 to 500 nM. It may be administered in a single dose or divided doses per day.

In addition, an antiviral agent of the present invention may be administered to a subject in need of treatment by various methods known in the art. The route of administration can be appropriately selected by taking into consideration the factors such as administration method, volume of body fluid and viscosity, etc.

The present invention provides a method for treating a viral disorder which comprises administering an RNA oligonucleotide to a subject in need of such treatment, wherein the RNA oligonucleotide comprises the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein the base sequences are bound to each other by a complementary binding to form double strands having a helical bend structure; and the base sequences represented by SEQ ID NO:1 and SEQ ID NO:2 have a hydroxy (OH) group at the 5'-end thereof.

Also the present invention provides a method for treating a viral disorder which comprises administering an RNA oligonucleotide to a subject in need of such treatment, wherein the RNA oligonucleotide comprises the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

Also the present invention provides a method for treating a viral disorder which comprises administering an RNA oligonucleotide to a subject in need of such treatment, wherein the RNA oligonucleotide comprises the base sequence represented by SEQ ID NO:17 (5'-$N_1$GUAGAN$_2$N$_3$N$_4$N$_5$UUUGCN$_6$-3') formed by connecting the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein two base sequences represented by SEQ ID NO:17 are bound to each other by a complementary binding to form double strands having a helical bend structure; and the base sequence represented by SEQ ID NO:17 has a hydroxy (OH) group at the 5'-end thereof.

Also the present invention provides a method for treating a viral disorder which comprises administering an RNA oligonucleotide to a subject in need of such treatment, wherein the RNA oligonucleotide comprises the base sequence represented by SEQ ID NO:17 (5'-$N_1$GUAGAN$_2$N$_3$N$_4$N$_5$UUUGCN$_6$-3') formed by connecting the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein first and second base sequences represented by SEQ ID NO:17 are bound to each other by a complementary binding to form double strands having a helical bend structure; the 3'-end of the first base sequence represented by SEQ ID NO:17 and the 5'-end of the second base sequence represented by SEQ ID NO:17 are connected into a loop to form a hairpin structure; and the first base sequence represented by SEQ ID NO:17 has a hydroxy (OH) group at the 5'-end thereof.

The RNA oligonucleotide is as described above. The subject may be a mammal, particularly, a human. The viral disorder may be a disorder caused by a DNA or RNA virus, the specific examples of which are as described above.

Also the present invention provides use of an RNA oligonucleotide for the preparation of a therapeutic agent for a viral disorder, wherein the RNA oligonucleotide comprises the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein the base sequences are bound to each other by a complementary binding to form double strands having a helical bend structure; and the base sequences represented by SEQ ID NO:1 and SEQ ID NO:2 have a hydroxy (OH) group at the 5'-end thereof.

Also the present invention provides use of an RNA oligonucleotide for the preparation of a therapeutic agent for a viral disorder, wherein the RNA oligonucleotide comprises the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

Also the present invention provides use of an RNA oligonucleotide for the preparation of a therapeutic agent for a viral disorder, wherein the RNA oligonucleotide comprises the base sequence represented by SEQ ID NO:17 (5'-$N_1$GUAGAN$_2$N$_3$N$_4$N$_5$UUUGCN$_6$-3') formed by connecting the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein two base sequences represented by SEQ ID NO:17 are bound to each other by a complementary binding to form double strands having a helical bend structure; and the base sequence represented by SEQ ID NO:17 has a hydroxy (OH) group at the 5'-end thereof.

Also the present invention provides use of an RNA oligonucleotide for the preparation of a therapeutic agent for a viral disorder, wherein the RNA oligonucleotide comprises the base sequence represented by SEQ ID NO:17 (5'-$N_1$GUAGAN$_2$N$_3$N$_4$N$_5$UUUGCN$_6$-3') formed by connecting the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein first and second base sequences represented by SEQ ID NO:17 are bound to each other by a complementary binding to form double strands having a helical bend structure; the 3'-end of the first base sequence represented by SEQ ID NO:17 and the 5'-end of the second base sequence represented by SEQ ID NO:17 are connected into a loop to form a hairpin structure; and the first base sequence represented by SEQ ID NO:17 has a hydroxy (OH) group at the 5'-end thereof.

The RNA oligonucleotide is as described above. The viral disorder may be a disorder caused by a DNA or RNA virus, the specific examples of which are as described above.

BEST MODE

Hereinafter, the present invention is explained in detail by Examples. The following Examples are intended to further illustrate the present invention without limiting its scope.

EXAMPLE 1

Preparation of RNA Oligonucleotides

RNA oligonucleotides which can increase the expression of interferon-β or ISG56 were prepared.

First, RNA oligonucleotides composed of the base sequence represented by SEQ ID NO:5 or SEQ ID NO:6 which have a triphosphate group at the 5'-end were prepared by the techniques known in the art. On the other hand, RNA oligonucleotides composed of one of the base sequences represented by SEQ ID NOS:5 to 10 and SEQ ID NOS:18 to 20 which have a hydroxy (OH) group at the 5'-end, or RNA oligonucleotides wherein a phosphodiester bond is substituted with a phosphorothioate bond were custom-made at Integrated DNA Technologies or Dharmacon.

As shown in FIG. 1, 5'-OH-control and 5'-PPP-control RNA oligonucleotides were prepared, which are composed of the base sequence represented by SEQ ID NO:5. They have a hydroxy group and a triphosphate group at the 5'-ends, respectively. In addition, 5'-OH-iav and 5'-PPP-iav RNA oligonucleotides were prepared, which are composed of the base sequence represented by SEQ ID NO:6, and have a hydroxy group and a triphosphate group at the 5'-ends, respectively. In addition, 5'-OH-Int-NS1 and 5'-OH-Bend-GC RNA oligonucleotides were prepared, which are composed of the base sequence represented by SEQ ID NO:7 or 8, respectively and have a hydroxy group at the 5'-ends. In addition, 5'-OH-Cont-GC-8 bp RNA oligonucleotide was prepared, which is composed of the base sequence represented by SEQ ID NO:9 and has a hydroxy group at the 5'-end. In addition, 5'-OH-Cont-GC-8 bp-PS RNA oligonucleotide was prepared by substituting the phosphodiester bonds constituting 5'-OH-Cont-GC-8 bp RNA oligonucleotide with phosphorothioate bonds. In addition, 5'-OH-Bend-GC-8 bp RNA oligonucleotide composed of the base sequence represented by SEQ ID NO:10 and having a hydroxy group at the 5'-end was prepared. In addition, 5'-OH-Bend-GC-8 bp-PS RNA oligonucleotide was prepared by substituting the phosphodiester bonds constituting the 5'-OH-Bend-GC-8 bp RNA oligonucleotide with phosphorothioate bonds. In addition, 5'-OH-8 bp-Bend-GC-Minimum RNA oligonucleotide was prepared, which is composed of the base sequences of SEQ ID NO:3 and SEQ ID NO:4, wherein each of the base sequences has a hydroxy group at the 5'-end and the bases are bound to each other by a complementary binding to form double strands. In addition, 5'-OH-16mer-Double-Bend-RNA oligonucleotide was prepared, wherein two base sequences represented by SEQ ID NO:18 are bound to each other by a complementary binding to form double strands and each of the base sequences represented by SEQ ID NO:18 has a hydroxy (OH) group at the 5'-end. In addition, 5'-OH-Long_Bend RNA oligonucleotide was prepared, which is composed of the base sequence represented by SEQ ID NO:19, and has a hydroxy group at the 5'-end. In addition, 5'-OH-Long_Bend-BPS RNA oligonucleotide was prepared by substituting part of phosphodiester bonds constituting the 5'-OH-Long_Bend RNA oligonucleotide with phosphorothioate bonds as shown in FIG. 1. In addition, 5'-OH-Long_Bend Short RNA oligonucleotide was prepared, which is composed of the base sequence represented by SEQ ID NO:20 and has a hydroxy group at the 5'-end.

EXAMPLE 2

Verification of Structure of RNA Oligonucleotides

To verify the structures of the 5'-OH-iav and 5'-PPP-iav RNA oligonucleotides prepared in Example 1, the following experiments were carried out.

First, the RNA oligonucleotides prepared in Example 1 were dissolved in a buffer solution containing 10 mM sodium phosphate (pH 6.5), 0.01 mM EDTA, 10 (v/v) % $D_2O$ to prepare a sample, and various spectroscopic experiments were carried out by the methods known in the art. More particularly, two-dimensional NOE spectroscopy (NOESY) was carried out by a nuclear magnetic resonance (NMR) spectroscope (Bruker, USA) of 400, 600 and 800 MHz with the mixing time of 100 and 200 ms. Also, the following experiments were performed: $^1H$-$^{15}N$ heteronuclear single quantum coherence (HSQC) spectroscopic experiment at the temperature of 278 K, double quantum filtered correlated (DQF-COSY) and homonuclear total correlation (TOCSY) spectroscopic experiments with the mixing time of 125 ms, $^1H$-$^{31}P$ heteronuclear correlation (HET-COR) and $^1H$-$^{31}P$ Hetero-TOCSY spectroscopic experiments with the mixing time of 30 ms, and NOESY spectroscopic experiment with the mixing time of 80, 150 and 250 ms. In addition, $^1H$-$^{13}C$ CT-HSQC, HCCH-COSY, 2D HCCH-relayed COSY, 2D HCCH-TOCSY and 3D HCCH-TOCSY spectroscopic experiments were carried out.

As a result of the NMR spectroscopic experiments, the NMR peaks of hydrogens of bases of the RNA oligonucleotides and H1', H2', H3', H4', and H5'/H5" were determined. From the NOESY spectroscopic experiment, approximately 563 NOE distance constraints were obtained, which were divided into 3 to 4 groups according to the distance (e.g., 1.8 to 3.4 Å, 1.8 to 5.0 Å and 3.8 to 7.0 Å; or 1.8 to 3.4 Å, 2.5 Å to 4.5, 3.5 to 6.0 Å and 4.0 to 7.0 Å). As for non-Watson-Crick bonds, no constraints on the hydrogen bonds were used. From the $^3J_{H1', H2'}$ value obtained in DQF-COSY, δ dihedral angle was obtained, and every X dihedral angle was fixed at −158±15 degrees. Other dihedral angles (for example, α, β, γ, ε, and ζ) were confined to the A-type helical structure of RNA. As for bulge parts, no constraints on the dihedral angles were used except for several β and ε dihedral angles. Residual dipolar coupling values were measured by HSQC experiment whose sensitivity was increased to reach the accuracy of ±1 Hz. In addition, by analyzing the result of the alignment tensor by singular value decomposition, the anisotropy value of −8.0 Hz and the rhombicity value of 0.32 were obtained. Calculation of every structure was carried out by X-PLOR 3.1 and CNS. 100 structures were generated according to the distance constraints, and simulated annealing process was carried out in which the structures were simulated at 3,000 K for 10 ps, and then cooled at 300 K for 50 ps. The distance force constant was kept at 50 kcal/mol/Å, and the dihedral angle constant was changed from 20 kcal/mol/Å to 400 kcal/mol/Å. The structures with the lowest energy state were purified at 300 K for 20 ps, and the last 5 ps were used for a restrained energy minimization. A total of 220 structures obtained from the above procedure were purified by adding 22 residual dipolar coupling values, with the force constant of the residual dipolar coupling value being kept to 3.0 kcal/mol. Ultimately, 32 structures were obtained, which were analyzed by Insight II (Biosym Technologies, USA) and CURVES 5.2 software.

Figure 2:
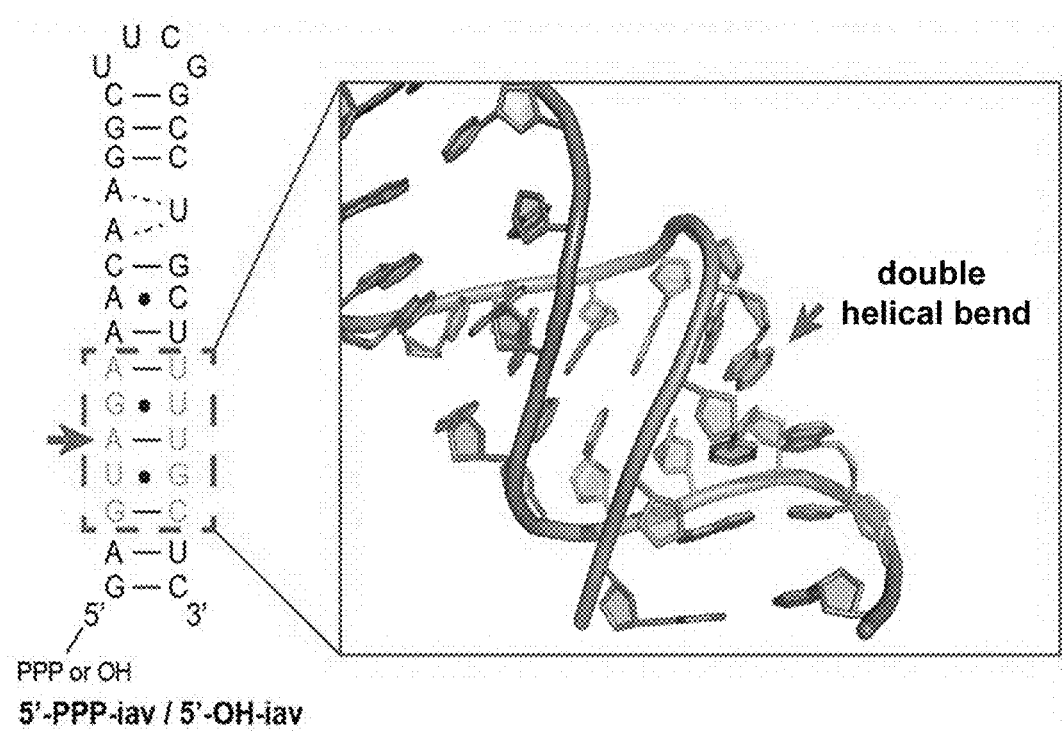
FIG. 2 shows the structure of 5'-OH-iav or 5'-PPP-iav, an RNA oligonucleotide prepared according to an example of the present invention.

As a result, as shown in FIG. 2, it was found that 5'-PPP-iav and 5'-OH-iav RNA oligonucleotides form a helical bend structure. Such a helical bend structure was found to be generated by the formation of double strands through non-Watson-Crick base pairing between two single strands which are respectively composed of the sequences represented by 5'-GUAGA-3' and 5'-UUUGC-3' in the 5'-PPP-iav and 5'-OH-iav RNA oligonucleotides. Thus, it was understood that the RNA oligonucleotides of the present invention comprising the sequences represented by 5'-GUAGA-3' and 5'-UUUGC-3', such as 5'-OH-Int-NS1, 5'-OH-Bend-GC, 5'-OH-Bend-GC-8 bp, 5'-OH-Bend-GC-8 bp-PS, 5'-OH-8 bp-Bend-GC-Minimum, 5'-OH-16mer-Double Bend, 5'-OH-Long_Bend, 5'-OH-Long_Bend-BPS, and 5'-OH-Long_Bend short RNA oligonucleotides also form a helical bend structure.

EXPERIMENTAL EXAMPLE 1

Verification of Interferon-β Expression by RNA Oligonucleotides

It was elucidated whether RNA oligonucleotides having a helical bend structure prepared in Example 1 can increase the expression of interferon-β.

1.1. Preparation of Cell Line

First, $3 \times 10^6$ of HEK293T cells (ATCC, USA) were aliquoted into 7 ml of Dulbecco's modified Eagle's medium (DMEM) supplemented with 10% fetal bovine serum (FBS, Gibco, USA) in 100 mm tissue culture plates, and cultured for 24 hours under the condition of 37° C. and 5% $CO_2$ to prepare a cell line.

1.2. Treatment with RNA Oligonucleotides

The cell line prepared in Experimental Example 1.1. was treated with the RNA oligonucleotides prepared in Example 1.

First, the cultured cells were detached by treatment with trypsin-EDTA (Gibco, USA) and the detached cells were counted and aliquoted into 6-well plates at $1 \times 10^3$ cells/well. Then, the cells were cultured for 42 hours under the condition of 37° C. and 5% $CO_2$. After removing the medium, the cells were treated with 400 μl of OPTI-MEM without FBS, and the RNA oligonucleotides.

RNA oligonucleotide treatment was as follows: 1 μM of 5'-PPP-control, 5'-PPP-iav, 5'-OH-control, 5'-OH-iav, 5'-OH-Int-NS1 or 5'-OH-Bend-OH-GC was mixed with 4 μl of lipofectamine LTX and 1.6 μl of plus-reagent, and 200 μl of resulting mixtures were added to the cells, respectively. Thereafter the cells were incubated for 4 hours under the condition of 37° C. and 5% $CO_2$. The cells for positive control were treated with poly (I:C), known as RIG-I ligand, and those for negative control were treated with culture medium only. After 4 hours, culture medium was removed, and 2 ml of DMEM containing 10% FBS was added to the cells, which were then further incubated for 2 hours under the condition of 37° C. and 5% $CO_2$.

1.3. Verification of Interferon-β Expression

To verify the expression of interferon-β in the cells treated with RNA oligonucleotides described above, RNA was isolated according to the following method.

After removing the culture medium, the cells were recovered with 500 μl of TRI-reagent (Ambion, USA), and chloroform was added to the collected cells to separate the RNA layer. Isopropanol was added thereto to make a pellet, and the pellet was washed with 75% ethanol, dried, and dissolved in sterilized distilled water. The separated RNAs were treated with DNase (Promega, USA) for 30 minutes at room temperature to remove contaminated DNAs, and DNase was inactivated by a stop solution. Then, the resultant was treated with Superscript III Reverse Transcriptase (Invitrogen, USA) for 1 hour at 50° C. to synthesize cDNAs from the RNAs.

Using the synthesized cDNA as a template, real-time PCR was carried out. Specifically, real-time PCR was carried out by mixing h-tag DNA polymerase (solgent, Republic of Korea), dNTP, tetraethylammonium chloride, evagreen dye (Biotium, USA), and primers for interferon-β target gene and GAPDH reference gene. Real-time PCR was performed as follows: fixation for 15 minutes at 95° C., then, repeating a set of reactions (20 seconds at 95° C., 40 seconds at 60° C., and 20 seconds at 72° C.) for 40 cycles. The primers for interferon-β and GAPDH are shown in Table 1 below.

TABLE 1

| SEQ ID NO | Name | Sequence |
|---|---|---|
| SEQ ID NO: 11 | Interferon-β forward | 5'-ggaggacgccgcattgac-3' |
| SEQ ID NO: 12 | Interferon-β reverse | 5'-caatagtctcattccagccagtgc-3' |
| SEQ ID NO: 13 | GAPDH forward | 5'-gcattgccctcaacgaccac-3' |
| SEQ ID NO: 14 | GAPDH reverse | 5'-gaggccatgtgggccatgag-3' |
| SEQ ID NO: 15 | ISG56 forward | 5'-gcctccttgggttcgtctacaa-3' |
| SEQ ID NO: 16 | ISG56 reverse | 5'-tcaaagtcagcagccagtctca-3' |

Figure 3:
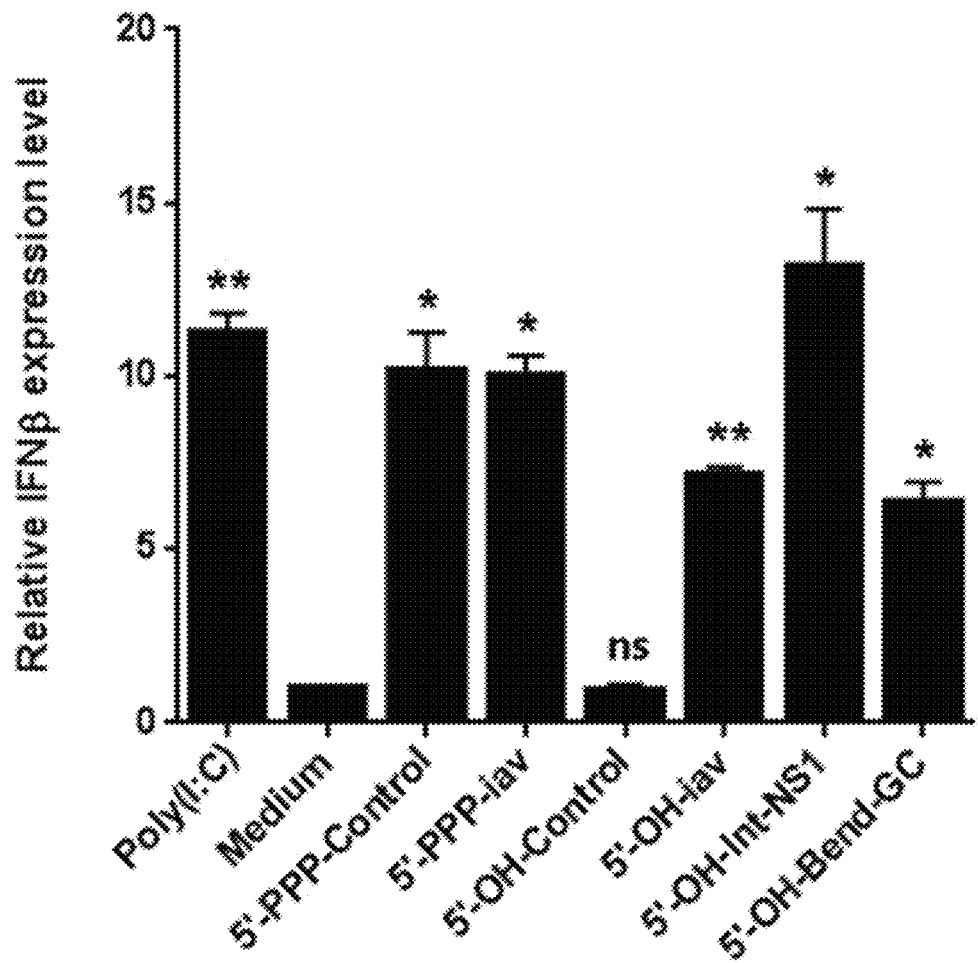
FIG. 3 is a graph showing the increase of interferon-β expression by RNA oligonucleotides prepared according to an example of the present invention.

The changes in the interferon-β expression are shown in the graph of FIG. 3.

As shown in FIG. 3, it was found that RNA oligonucleotides having a helical bend structure even with a hydroxy group at the 5'-end, such as 5'-OH-Int-NS1 and 5'-OH-Bend-GC, increased the interferon-β expression to a significant level, as well as RNA oligonucleotides having a triphosphate group at the 5'-end.

EXPERIMENTAL EXAMPLE 2

Verification of Interferon-β Expression by Short-length Hairpin RNA

In Experimental Example 1, it was found that RNA oligonucleotides having a helical bend structure increased the interferon-β expression. To elucidate which portion of the RNA oligonucleotides influences the interferon-β expression, a real time PCR was performed by the same method as Experimental Example 1 using 5'-OH-Bend-GC-8 bp, which is a shorter hairpin RNA containing a helical bend structure.

The cells for negative control were treated with the culture medium only or 5'-OH-control, while those for positive control were treated with poly (I:C). The cells of experimental groups were treated with 5'-OH-Bend-GC-8 bp and 5'-OH-Bend-GC RNA oligonucleotides. The experiments with 5'-OH-Bend-GC-8 bp were performed three times.

Figure 4:
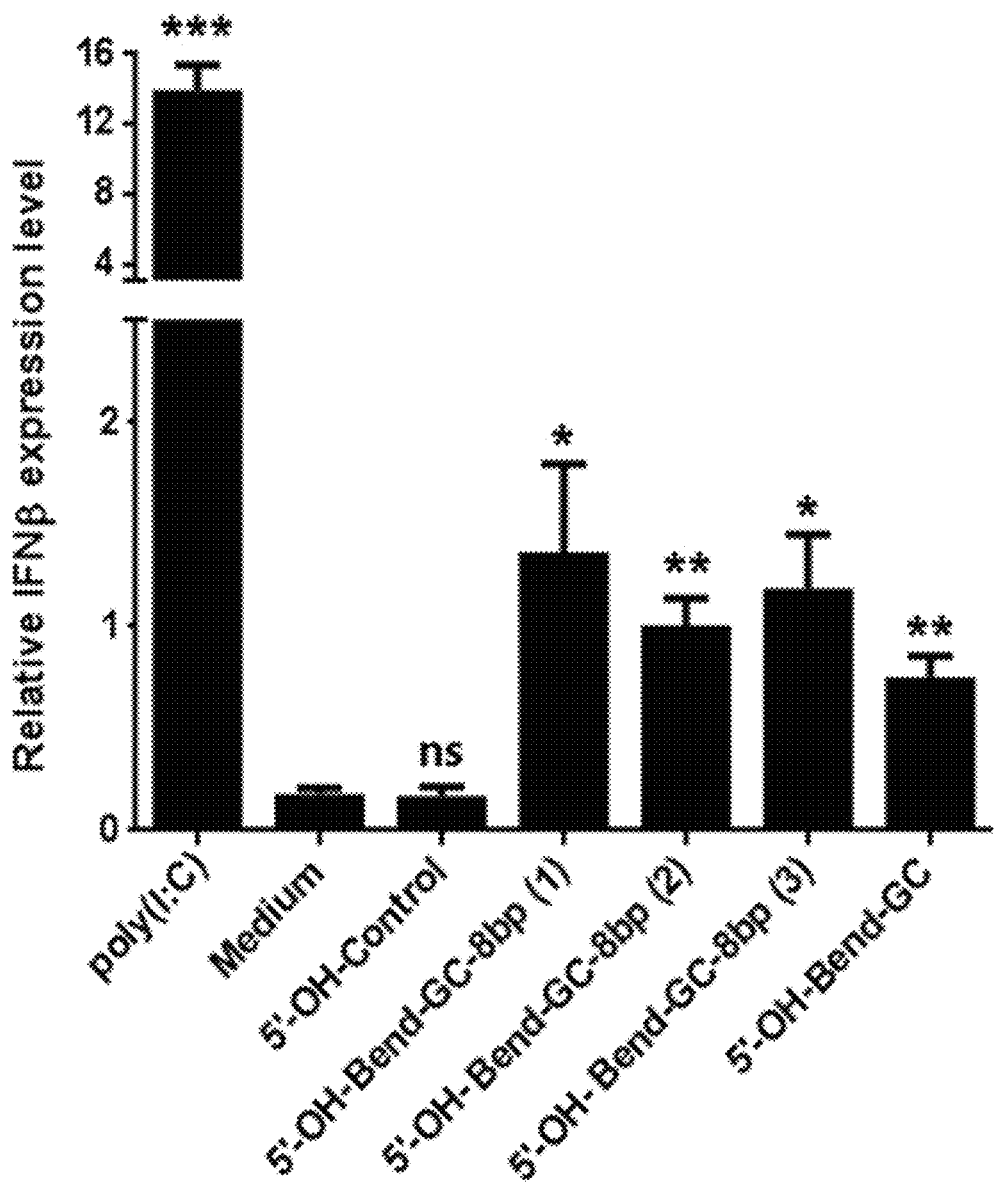
FIG. 4 is a graph showing the increase of interferon-β expression by 5'-OH-Bend-GC-8 bp, an RNA oligonucleotide prepared according to an example of the present invention.

The changes in the interferon-β expression are shown in the graph of FIG. 4.

As shown in FIG. 4, it was found that 5'-OH-Bend-GC-8 bp and 5'-OH-Bend-GC increased the interferon-β expression to a significant level.

EXPERIMENTAL EXAMPLE 3

Verification of ISG56 Expression by Minimum-length RNA Oligonucleotide

To elucidate whether 5'-OH-8 bp-Bend-GC-Minimum, a double-stranded RNA of minimum length excluding the loop portion of 5'-OH-Bend-GC-8 bp verified in Experimental Example 2, can increase the interferon-β expression, changes in ISG56 expression which is induced by interferon-β expression were examined.

All experiments were performed by the same method as Experimental Example 1 using the primers shown in Table 1, except the following. The cells for negative control were treated with the culture medium only or 5'-OH-Cont-GC-8 bp having no helical bend structure, while those for positive control were treated with 5'-PPP-Control. The cells of experimental groups were treated with 5'-OH-Bend-GC-8 bp and 5'-OH-8 bp-Bend-GC-Minimum RNA oligonucleotides.

Figure 5:
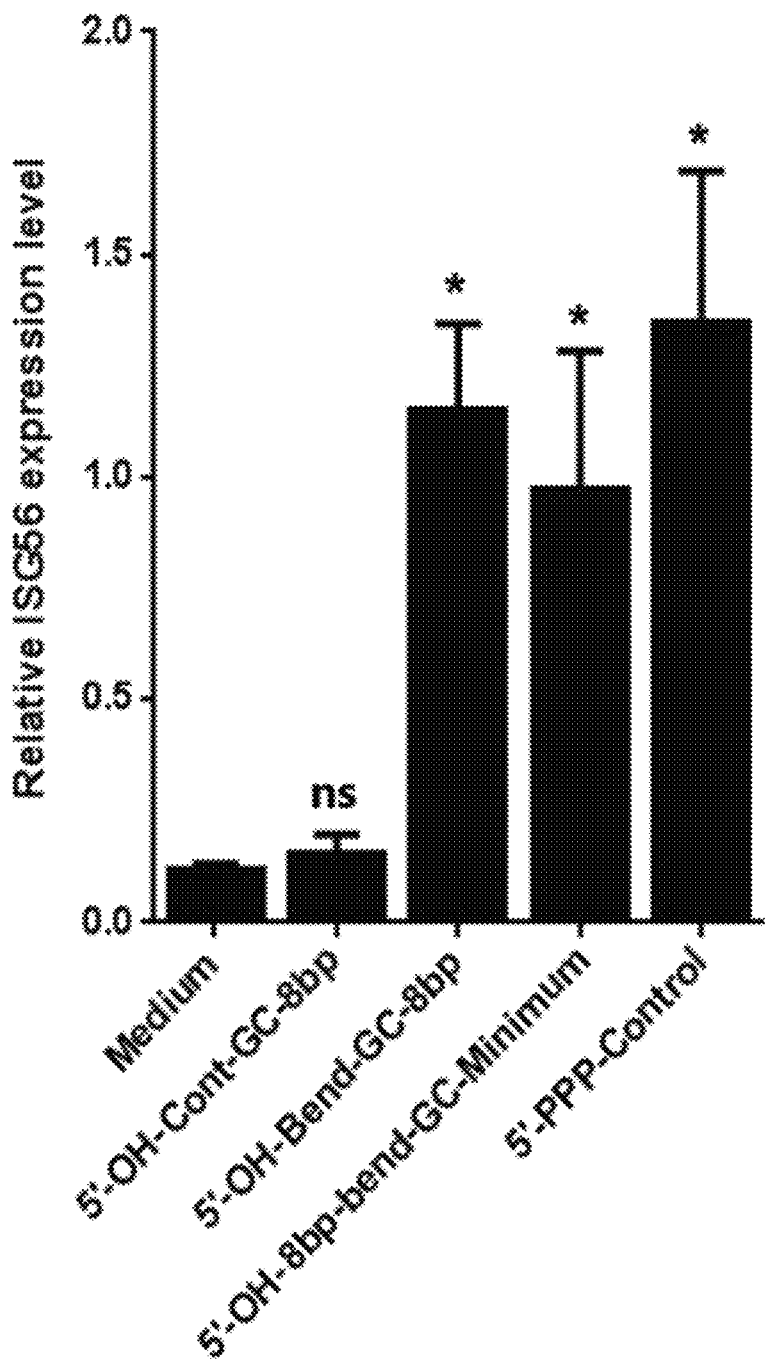
FIG. 5 is a graph showing the increase of ISG56 expression by 5'-OH-8 bp-Bend-GC Minimum, an RNA oligonucleotide prepared according to an example of the present invention.

The changes in the ISG56 expression are shown in the graph of FIG. 5.

As shown in FIG. 5, it was found that 5'-OH-8 bp-Bend-GC-Minimum (a minimum-length double-stranded RNA oligonucleotide in which the base sequences represented by SEQ ID NO:3 and SEQ ID NO:4 are bound by a complementary binding) increased the ISG56 expression to a significant level.

EXPERIMENTAL EXAMPLE 4

Verification of ISG56 Expression by RNA Oligonucleotides Connected by Phosphorothioate Bond or Palindromic Structure Among the RNA oligonucleotides prepared above having a helical bend structure, an RNA oligonucleotide (5'-OH-Bend-GC-8 bp-PS) in which the phosphodiester bonds are substituted with phosphorothioate bonds or an RNA oligonucleotide (5'-OH-16mer-Double-Bend) having two helical bend structures in which two minimum-length RNA oligonucleotides having a helical bend structure are connected by a palindromic structure were tested to examine whether these RNA oligonucleotides can increase the interferon-β expression by assessing changes in the ISG56 expression induced by interferon-β expression.

All experiments were performed by the same method as Experimental Example 1 using the primers shown in Table 1, except the following. The cells for negative control were treated with the culture medium only or 5'-OH-Cont-GC-8 bp having no helical bend structure, while those for positive control were treated with 5'-OH-Bend-GC-8 bp. The cells of experimental groups were treated with 5'-OH-Bend-GC-8 bp-PS and 5'-OH-16mer-Double Bend RNA oligonucleotides.

Figure 6:
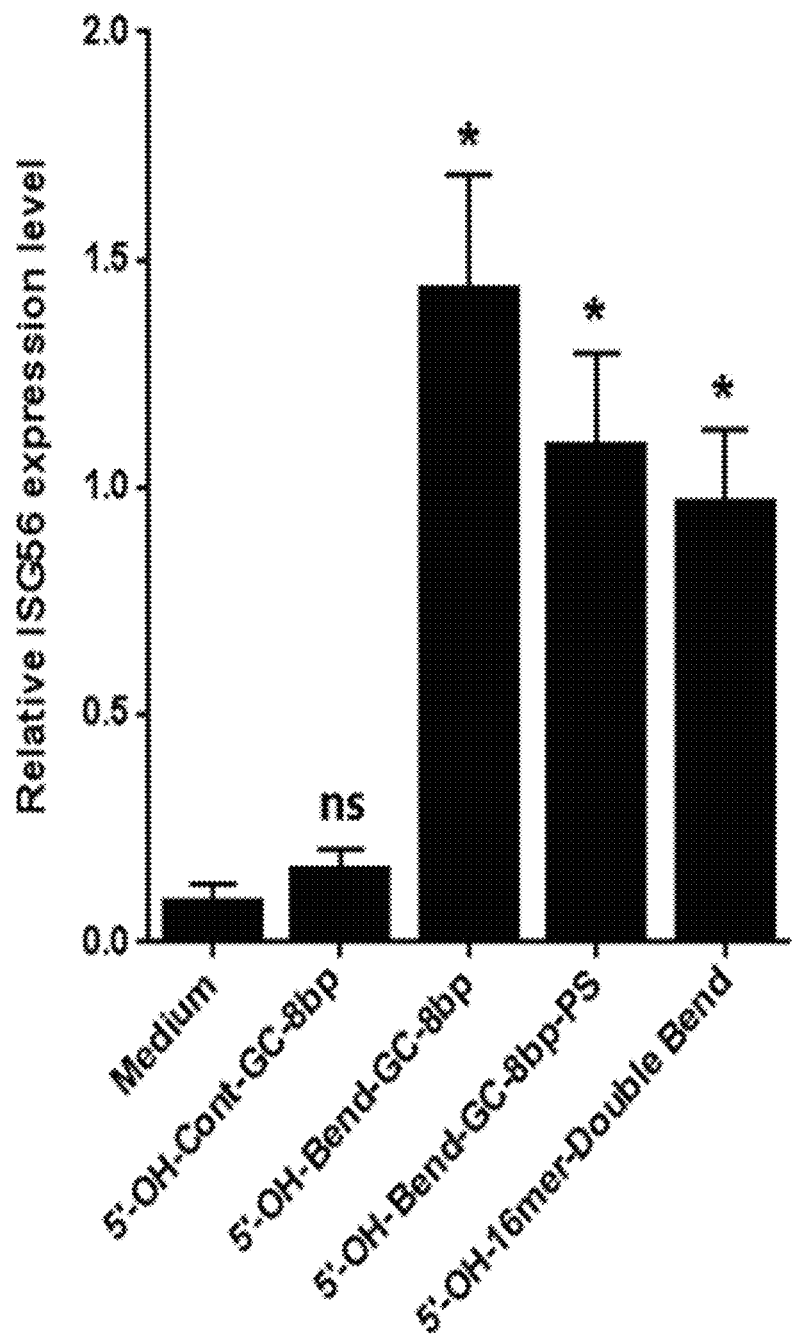
FIG. 6 is a graph showing the increase of ISG56 expression by 5'-OH-Bend-GC-8 bp, 5'-OH-Bend-GC-8 bp-PS and 5'-OH-16mer-Double Bend, RNA oligonucleotides prepared according to an example of the present invention.

The changes in the ISG56 expression are shown in the graph of FIG. 6.

As shown in FIG. 6, it was found that 5'-OH-Bend-GC-8 bp-PS, an RNA oligonucleotide which has a helical bend structure and a resistance to endonuclease due to the substitution of a phosphodiester bond with a phosphorothioate bond, and 5'-OH-16mer-Double Bend increased the ISG56 expression to a significant level.

EXPERIMENTAL EXAMPLE 5

Verification of ISG56 Expression by Long-length RNA Oligonucleotide

Among the RNA oligonucleotides having a helical bend structure prepared above, it was examined whether a long-length RNA oligonucleotide (5'-OH-Long_Bend) can increase the interferon-β expression by assessing changes in the ISG56 expression which is induced by interferon-β expression.

All experiments were performed by the same method as Experimental Example 1 using the primers shown in Table 1, except the following. The cells for negative control were treated with the culture medium only, while those for positive control were treated with 5'-PPP-iav. The cells of experimental groups were treated with 5'-OH-Long_Bend RNA oligonucleotide.

Figure 7:
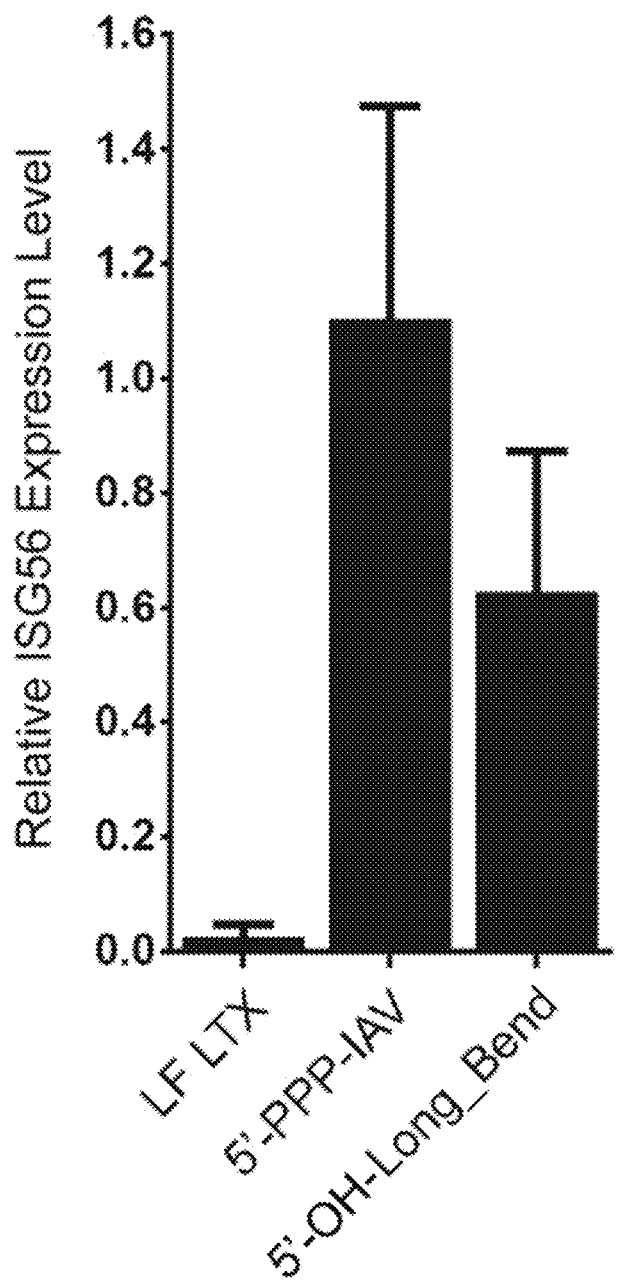
FIG. 7 is a graph showing the increase of ISG56 expression by 5'-OH-Long_Bend, an RNA oligonucleotide prepared according to an example of the present invention.

The changes in the ISG56 expression are shown in the graph of FIG. 7.

As shown in FIG. 7, it was found that 5'-OH-Long_Bend, a long-length RNA oligonucleotide having a helical bend structure, increased the ISG56 expression to a significant level.

EXPERIMENTAL EXAMPLE 6

Verification of ISG56 Expression by Long-length Hairpin RNA Part of which has Phosphorothioate Bonds Among the RNA oligonucleotides prepared above having a helical bend structure and a long-length hairpin, it was examined whether 5'-OH-Long_Bend-BPS RNA oligonucleotide, in which part of phosphodiester bonds forming the RNA oligonucleotide was substituted with phosphorothioate bonds, increases the interferon-β expression by assessing changes in the ISG56 expression.

All experiments were performed by the same method as Experimental Example 1 using the primers shown in Table 1, except the following. The cells for negative control were treated with the culture medium only or 5'-OH-Cont-GC-8 bp, while those for positive control were treated with 5'-OH-Bend-GC-8 bp and 5'-OH-Bend-GC-8 bp-PS. The cells of experimental group were treated with 5'-OH-Long_Bend-BPS RNA oligonucleotide.

Figure 8:
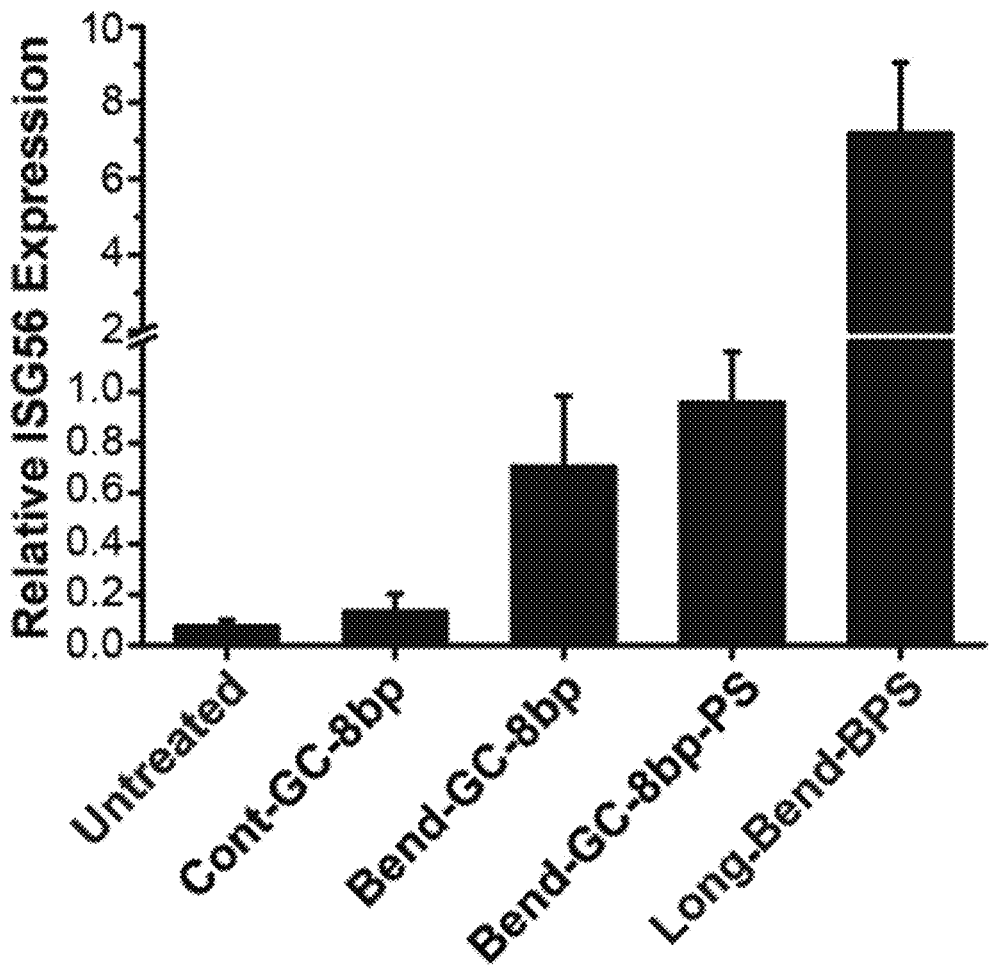
FIG. 8 is a graph showing the increase of ISG56 expression by 5'-OH-Long_Bend-BPS, an RNA oligonucleotide prepared according to an example of the present invention.

The changes in the ISG56 expression are shown in the graph of FIG. 8.

As shown in FIG. 8, it was found that 5'-OH-Long_Bend-BPS RNA oligonucleotide, which has a helical bend structure and a long-length hairpin wherein the bonds in a part of the RNA polynucleotide forming the bend structure were substituted with phosphorothioate bonds, increased the ISG56 expression to a significant level. Specifically, 5'-OH-Long_Bend-BPS showed about 7-fold increase in the ISG56 expression as compared to 5'-OH-Bend-GC-8 bp.

EXPERIMENTAL EXAMPLE 7

Verification of Antiviral Activity of RNA Oligonucleotides Having Phosphorothioate Bonds and Long-length Hairpin RNA To elucidate the antiviral activity of the RNA oligonucleotides having a helical bend structure, the following experiments were conducted.

7.1. Preparation of Influenza a Virus

Eggs embryonated for 10 days were infected with influenza A virus/Puerto Rico/8/34(H1N1)(PR8) (ATCC, USA) followed by amplification for 3 days at 37° C. The titers of the amplified viruses were examined by a plaque assay, and the resulting viruses were stored at −70° C.

Specifically, MDCK (Madin-Darby canine kidney; ATCC, USA) cell line cultured in MEM (minimum essential medium; Hyclone, USA) supplemented with 10% FBS (Gibco, USA) was aliquoted into a 48-well plate at $5\times10^5$ cells/well. The cells were cultured until the wells were filled with cells, and then the cells were added with and thus infected with 100 μl of influenza A virus which was 10-fold serially diluted in serum-free MEM. After maintaining infected cells for 1 hour at 37° C., the medium was removed and the cells were washed with PBS. Then, 0.2 ml of MEM supplemented with 0.5% carboxymethylcellulose (Sigma, USA) and 2 μg/ml TPCK-trypsin (Sigma, USA) was added thereto. After culturing the cells for 3 days at 33° C., the titer of viruses was assessed by staining the resulting plaques with 0.1% crystal violet.

7.2. Verification of Antiviral Activity-(1)

A549 (ATCC, USA) cell line cultured in RPMI1640 medium (Hyclone, USA) supplemented with 10% FBS was aliquoted into 6-well plates at $1\times10^6$ cells/well. Next day, the cells of experimental groups were transfected with 5'-OH-Bend-GC-8 bp-PS or 5'-OH-Long_Bend RNA oligonucleotide at a concentration of 10, 30 or 100 nM. As a negative control, cells were treated with 5'-OH-Cont-GC-8 bp without having a helical bend structure at a concentration of 100 nM, while those for positive control were treated with 0.1 μg/ml poly I:C (polyinosine-polycytidylic acid) or 2 μM oseltamivir (OSV-C; Sigma, USA). Transfection was carried out by using Lipofectamine 2000 (Invitrogen, USA) according to the manufacturer's protocol. After 24 hours, the culture media were removed, and the cells were infected with the influenza A viruses prepared in Experimental Example 7.1. at 0.1 MOI. After maintaining the cells for 1 hour at 37° C., the medium was removed, and the cells were treated with RPMI1640 medium supplemented with 0.1 μg/ml TPCK-trypsin for 1 day. Thereafter, the cells were dissolved by adding 0.3 ml of M-PER solution (Thermo Scientific, USA) to the wells, and Western blot was carried out by a conventional method using the cell lysates.

Specifically, the protein contained in the cell lysates was quantified, and loaded at 30 μg/well on 10% SDS-PAGE gel to perform electrophoresis. The electrophoresed protein was transferred to PVDF membrane (Immobilion-P membrane; Millipore, USA), and pre-treated with 1×PBS containing 5% BSA for 1 hour at room temperature. Then the membrane was washed with 1×PBS, and reactions were carried out with a primary antibody overnight at 4° C., and then with a secondary antibody for 1 hour at room temperature. In this connection, anti-NP antibody (11675-MM03, Sino Biological, China) and HRP-bound goat anti-mouse IgG (Sigma-Aldrich, USA) were used for the detection of viral NP protein. Meanwhile, anti-NS1 antibody (sc-17596, Santa Cruz Biotechnology, USA) and HRP-bound donkey anti-goat IgG (Sigma-Aldrich, USA) were used for the detection of viral NS1 protein. As a control group, the level of β-actin expression was examined by using anti-β-actin antibody (Sigma-Aldrich, USA) and HRP-bound goat anti-mouse IgG (Sigma-Aldrich, USA). Protein bands were examined by using SuperSignal West Pico Chemiluminescent Substrate (Pierce, USA), and the images of results obtained by LAS-4000 (Fujifilm, Japan) image analyzer are shown in FIG. 9A.

As shown in FIG. 9A, it was found that 5'-OH-Bend-GC-8 bp-PS and 5'-OH-Long_Bend RNA oligonucleotides showed antiviral activity against influenza A virus in a concentration-dependent manner. Especially, 5'-OH-Long_Bend RNA oligonucleotide showed an excellent effect corresponding to the positive control group (poly I:C), even at a low concentration of 10 nM.

7.3. Verification of Antiviral Activity-(2)

Cells were prepared by a same method as Experimental Example 7.2., and then transfected with RNA oligonucleotides. As a negative control, cells were treated with 5'-OH-Cont-GC-8 bp without having a helical bend structure at a concentration of 100 nM, while those for positive control were treated with 0.1 μg/ml poly I:C (polyinosine-polycytidylic acid) or 10 μM oseltamivir (OSV-C; Sigma, USA).

24 hours after the transfection, the culture medium was removed. The influenza A viruses prepared in Experimental Example 7.1. were 100-fold diluted and the cells were infected with such diluted viruses. After maintaining the cells for 1 hour at 37° C., the medium was removed again, and cells with RPMI1640 medium supplemented with 0.1 μg/ml TPCK-trypsin were cultured. After 24-hour culture, MDCK cell line was infected with the resultant cell medium by a same method as Experimental Example 7.1. to assess the titer of viruses.

The photograph of cells stained with crystal violet and the titer of viruses are shown in FIG. 9B.

As shown in FIG. 9B, it was found that 5'-OH-Bend-GC-8 bp-PS and 5'-OH-Long_Bend RNA oligonucleotides showed antiviral activity against influenza A virus in a concentration-dependent manner. Especially, like the Western blot results described above, 5'-OH-Long_Bend RNA oligonucleotide showed an excellent effect corresponding to the positive control group (poly I:C) even at a low concentration of 10 nM.

7.4. Verification of Antiviral Activity-(3)

The antiviral activity of RNA oligonucleotides was examined by a same method as Experimental Example 7.2. except that the cells of experimental groups were treated with 5'-OH-Long_Bend or 5'-OH-Long_Bend Short RNA oligonucleotide at various concentrations. As a negative control, cells were treated with 5'-OH-Cont-GC-8 bp without having a helical bend structure at a concentration of 100 nM, while those for positive control were treated with 100 nM of 5'-OH-Bend-GC-8 bp-PS RNA oligonucleotide.

As shown in FIG. 10, it was found that 5'-OH-Long_Bend RNA oligonucleotide and 5'-OH-Long_Bend Short RNA oligonucleotide inhibited the expression of viral proteins significantly as compared to the control group, at the concentrations of 10 nM or higher, and 100 nM, respectively.

7.5. Verification of Antiviral Activity-(4)

The antiviral activity of RNA oligonucleotides was examined by a same method as Experimental Example 7.2. except that the cells of experimental groups were treated with 5'-OH-Long_Bend-BPS RNA oligonucleotide at a concentration of 0.1, 1, 10, or 100 nM, As a negative control, cells were infected with viruses only or treated with 100 nM of 5'-OH-Cont-GC-8 bp or 5'-OH-Cont-GC-8 bp-PS without having a helical bend structure.

As shown in FIG. 11, it was found that 5'-OH-Long_Bend-BPS RNA oligonucleotide inhibited the expression of a viral protein significantly at a concentration of 1 nM or higher. This result indicates that an RNA oligonucleotide having a helical bend structure can be used as an active ingredient for an antiviral agent.

This application contains references to amino acid sequences and/or nucleic acid sequences which are being submitted concurrently herewith as the sequence listing text file 61877587.1, file size 4.93 KB KiloBytes (KB), created on 11 Nov. 2016. The aforementioned sequence listing is hereby incorporated by reference in its entirety.

What is claimed is:

1. An antiviral agent comprising an RNA oligonucleotide as an active ingredient, wherein the RNA oligonucleotide comprises the base sequence represented by SEQ ID NO:1 (5'-$N_1$GUAGA$N_2N_3$-3') and the base sequence represented by SEQ ID NO:2 (5'-$N_4N_5$UUUGC$N_6$-3'), wherein, the base sequences are bound to each other by a complementary binding to form double strands having a helical bend structure;

the base sequences represented by SEQ ID NO:1 and SEQ ID NO:2 have a hydroxy (OH) group at the 5'-end thereof; and wherein N1 to N6 in the base sequence represented by SEQ ID NO:1 and SEQ ID NO:2 are selected from the group consisting of A, G, C, and U.

2. The antiviral agent of claim 1, wherein $N_1$ to $N_6$ are G or C in the base sequence represented by SEQ ID NO:1 or SEQ ID NO:2.

3. The antiviral agent of claim 2, wherein $N_1$ is G, $N_2$ is C, and $N_3$ is G in the base sequence represented by SEQ ID NO:1 (corresponding to SEQ ID NO:3); and $N_4$ is C, $N_5$ is G, and $N_6$ is C in the base sequence represented by SEQ ID NO:2 (corresponding to SEQ ID NO:4).

4. An antiviral agent comprising an RNA oligonucleotide as an active ingredient, wherein the RNA oligonucleotide comprises the base sequence represented by SEQ ID NO:1 (5'-$N_1$GUAGA$N_2N_3$-3') and the base sequence represented by SEQ ID NO:2 (5'-$N_4N_5$UUUGC$N_6$-3'), wherein the base sequences are bound to each other by a complementary binding to form double strands having a helical bend structure;

the 3'-end of the base sequence represented by SEQ ID NO:1 and the 5'-end of the base sequence represented by SEQ ID NO:2 are connected into a loop to form a hairpin structure;

the base sequence represented by SEQ ID NO:1 has a hydroxy (OH) group at the 5'-end thereof; and wherein $N_1$ to $N_6$ in the base sequence represented by SEQ ID NO:1 and SEQ ID NO:2 are selected from the group consisting of A, G, C, and U.

5. The antiviral agent of claim 4, wherein $N_1$ to $N_6$ are G or C in the base sequence represented by SEQ ID NO:1 or SEQ ID NO:2.

6. The antiviral agent of claim 5, wherein $N_1$ is G, $N_2$ is C, and $N_3$ is G in the base sequence represented by SEQ ID NO:1 (corresponding to SEQ ID NO:3); and $N_4$ is C, $N_5$ is G, and $N_6$ is C in the base sequence represented by SEQ ID NO:2 (corresponding to SEQ ID NO:4).

7. The antiviral agent of claim 4, wherein the loop is composed of at least 4 bases.

8. The antiviral agent of claim 7, wherein the loop is composed of UUCG bases.

9. The antiviral agent of claim 4, wherein the loop is composed of 4 to 80 bases.

10. The antiviral agent of claim 9, wherein the loop has a stem structure formed by Watson-Crick base pairing, and the stem structure comprises AU motif composed of AU base pairs.

11. The antiviral agent of claim 4, wherein the RNA oligonucleotide is a base sequence represented by SEQ ID NO:6, SEQ ID NO:7, SEQ ID NO:8, SEQ ID NO:10, SEQ ID NO:19 or SEQ ID NO:20.

12. An antiviral agent comprising an RNA oligonucleotide as an active ingredient, wherein the RNA oligonucleotide comprises the base sequence represented by SEQ ID NO:17 (5'-$N_1$GUAGA$N_2N_3N_4N_5$UUUGC$N_6$-3') formed by connecting the base sequence represented by SEQ ID NO:1 (5'-$N_1$GUAGA$N_2N_3$-3') and the base sequence represented by SEQ ID NO:2 (5'-$N_4N_5$UUUGC$N_6$-3'), wherein, two base sequences represented by SEQ ID NO:17 are bound to each other by a complementary binding to form double strands having a helical bend structure;

the base sequence represented by SEQ ID NO:17 has a hydroxy (OH) group at the 5'-end thereof; and wherein $N_1$ to $N_6$ in the base sequence represented by SEQ ID NO:17 are selected from the group consisting of A, G, C, and U.

13. The antiviral agent of claim 12, wherein $N_1$ to $N_6$ are G or C in the base sequence represented by SEQ ID NO:17.

14. The antiviral agent of claim 13, wherein $N_1$ is G, $N_2$ is C, $N_3$ is G, $N_4$ is C, $N_5$ is G, and $N_6$ is C in the base sequence represented by SEQ ID NO:17 (corresponding to SEQ ID NO:18).

15. The antiviral agent of claim 1, wherein at least one of the phosphodiester bonds in the RNA oligonucleotide is changed to at least one selected from the group consisting of a phosphorothioate bond, a boranophosphate bond and a methylphosphonate bond.

16. The antiviral agent of claim 1, wherein the antiviral agent has an antiviral activity against one selected from the group consisting of hepatitis C virus, Dengue virus, acute respiratory syndrome virus, Middle East respiratory syndrome coronavirus, influenza virus, West Nile virus, Ebola virus, vesicular stomatitis virus, Newcastle Disease virus, hepatitis B virus, and a combination thereof.

17. The antiviral agent of claim 4, wherein at least one of the phosphodiester bonds in the RNA oligonucleotide is changed to at least one selected from the group consisting of a phosphorothioate bond, a boranophosphate bond and a methylphosphonate bond.

18. The antiviral agent of claim 12, wherein at least one of the phosphodiester bonds in the RNA oligonucleotide is changed to at least one selected from the group consisting of a phosphorothioate bond, a boranophosphate bond and a methylphosphonate bond.

19. The antiviral agent of claim 4, wherein the antiviral agent has an antiviral activity against one selected from the group consisting of hepatitis C virus, Dengue virus, acute respiratory syndrome virus, Middle East respiratory syndrome coronavirus, influenza virus, West Nile virus, Ebola virus, vesicular stomatitis virus, Newcastle Disease virus, hepatitis B virus, and a combination thereof.

20. The antiviral agent of claim 12, wherein the antiviral agent has an antiviral activity against one selected from the group consisting of hepatitis C virus, Dengue virus, acute respiratory syndrome virus, Middle East respiratory syndrome coronavirus, influenza virus, West Nile virus, Ebola virus, vesicular stomatitis virus, Newcastle Disease virus, hepatitis B virus, and a combination thereof.

* * * * *